US00PP36683P2

(12) United States Plant Patent
Korlipara

(10) Patent No.: US PP36,683 P2
(45) Date of Patent: May 13, 2025

(54) KNIPHOFIA PLANT NAMED 'ROCKET JR.'

(50) Latin Name: ***Kniphofia* spp.**
Varietal Denomination: Rocket Jr.

(71) Applicant: Terra Nova Nurseries, Inc., Canby, OR (US)

(72) Inventor: Harini Korlipara, Tualatin, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 18/102,245

(22) Filed: Jan. 27, 2023

(51) Int. Cl.
*A01H 5/02* (2018.01)
*A01H 6/00* (2018.01)

(52) U.S. Cl.
USPC ..... Plt./443

(58) Field of Classification Search
USPC ..... Plt./443
CPC ..... A01H 5/02; A01H 5/00; A01H 6/00
See application file for complete search history.

(56) References Cited

U.S. PATENT DOCUMENTS

PP28,464 P2 * 9/2017 Egger ..... A01H 6/00
Plt./443

OTHER PUBLICATIONS

Ditoplant Export BV Tissue culture 2022 retrieved on May 10, 2023 at https://www.ditoplant.nl/?p=pagina&s=30&lang=en, pp. 1,17. (Year: 2022).*

* cited by examiner

*Primary Examiner* — June Hwu
(74) *Attorney, Agent, or Firm* — The Webb Law Firm

(57) ABSTRACT

A new and distinct *Kniphofia* plant characterized by characterized by its habit of forming multiple crowns fast and each crown produces inflorescences in the first season, inflorescences of bright red-orange and yellow flowers on short stems, a very long bloom time with repeat blooming, a short habit, excellent vigor, and narrow, grassy, and short leaves.

2 Drawing Sheets

Botanical classification: *Kniphofia* spp.
Varietal denomination: 'Rocket Jr.'.

BACKGROUND OF THE NEW PLANT

The present invention is a new and distinct *Kniphofia* plant having the varietal name 'Rocket Jr.'. *Kniphofia* is in the family Xanthorrhoeaceae. 'Rocket Jr.' is a hybrid resulting from a planned breeding program with the purposes of producing short, compact, and reblooming *Kniphofia* plants. The cross was made using the following proprietary, unpatented, and unreleased plants: *Kniphofia* plants K58-3, as the seed parent, and K69-1, as the pollen parent. The new cultivar, 'Rocket Jr.', was selected for having the best habit, flower color, reblooming quality, and crown count from many seedlings of the cross in Canby, Oregon.

Compared to *Kniphofia* plant K58-3, the seed parent, the new cultivar is shorter, more free-flowering, has larger floral racemes and a more distinct bicolored red to yellow color shift as the flowers age. A comparison to the pollen parent cannot be provided, as the pollen parent is extinct.

Compared to *Kniphofia* plant named 'Poco Sunset' (U.S. Plant Pat. No. 28,464), the new cultivar is shorter with shorter leaves in a denser habit. The flowers of the new cultivar are more red-orange and yellow rather than coral-red, fading to yellow and cream.

Compared to *Kniphofia* plant named 'Fire Glow' (U.S. Plant Pat. No. 22,894), the new cultivar has shorter leaves and inflorescences and has flowers that are red-orange and yellow rather than red-orange and coral.

The new variety has only been reproduced by asexual propagation (division and tissue culture). Each of the progeny exhibits identical characteristics to the original plant. Asexual propagation by division and tissue culture performed in Canby, Oregon shows that the characteristics and distinctions described herein come true to form and are established and transmitted through succeeding propagations. The present invention has not been evaluated under all possible environmental conditions. The phenotype may vary with variations in environment without a change in the genotype of the plant.

When compared to other *Kniphofia* plants known to the breeder, the new variety is characterized by the following:

1. Very stiff, upright habit, with well-spaced crowns that provide a more formal appearance;
2. Large inflorescences of bright red-orange and yellow to cream flowers on short stems;
3. A very long bloom time with repeat blooming from June through October in Canby, Oregon;
4. A short habit;
5. Narrow, short, and grassy leaves; and
6. Excellent vigor.

DESCRIPTION OF THE DRAWINGS

The accompanying photographic drawings illustrate the new variety, with the colors being as nearly true as possible with color illustrations of this type.

DETAILED BOTANICAL DESCRIPTION

Figure 1:
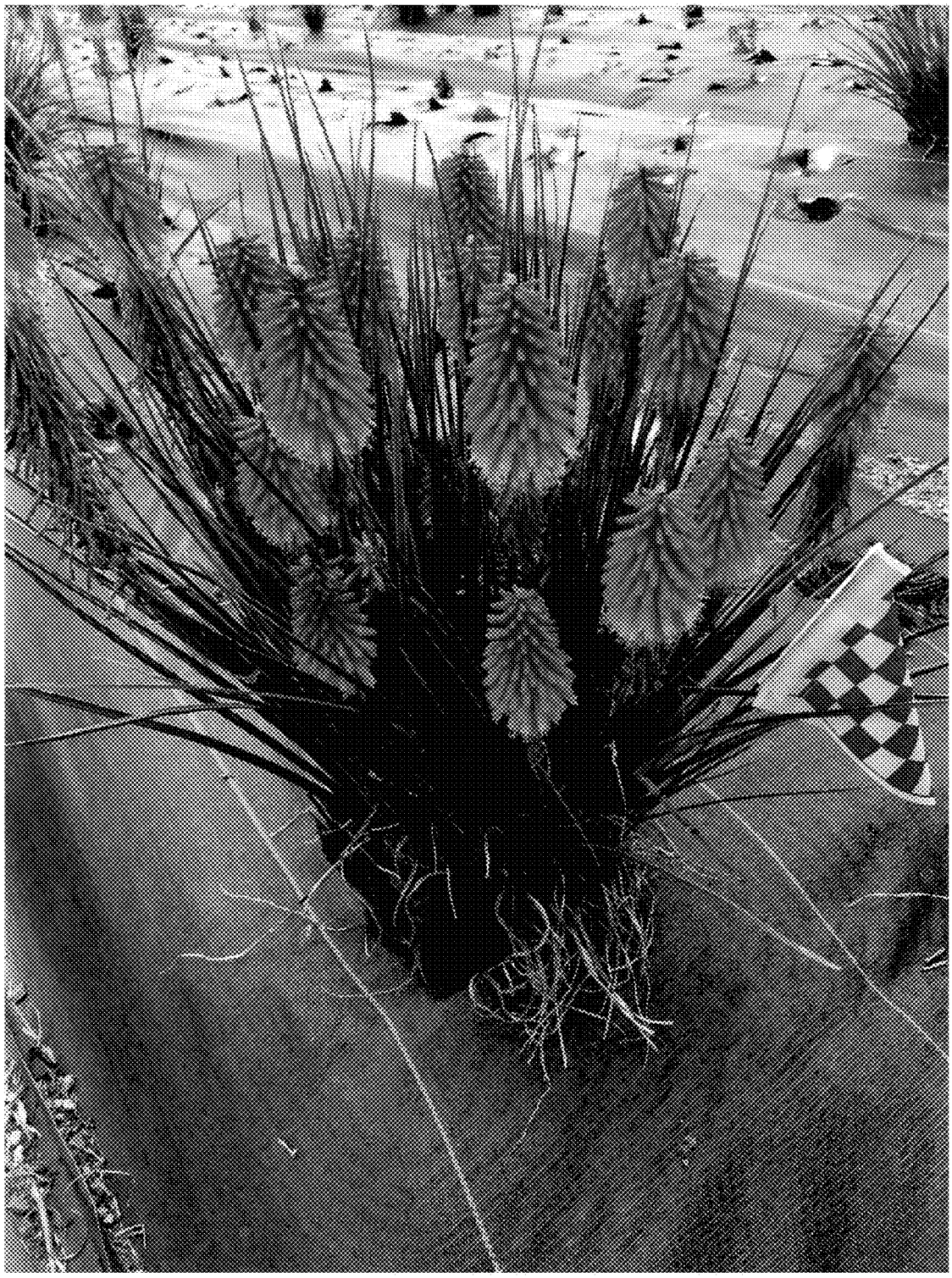
FIG. 1 illustrates an 18-month-old plant of the new variety in Canby, Oregon in July.
Figure 2:
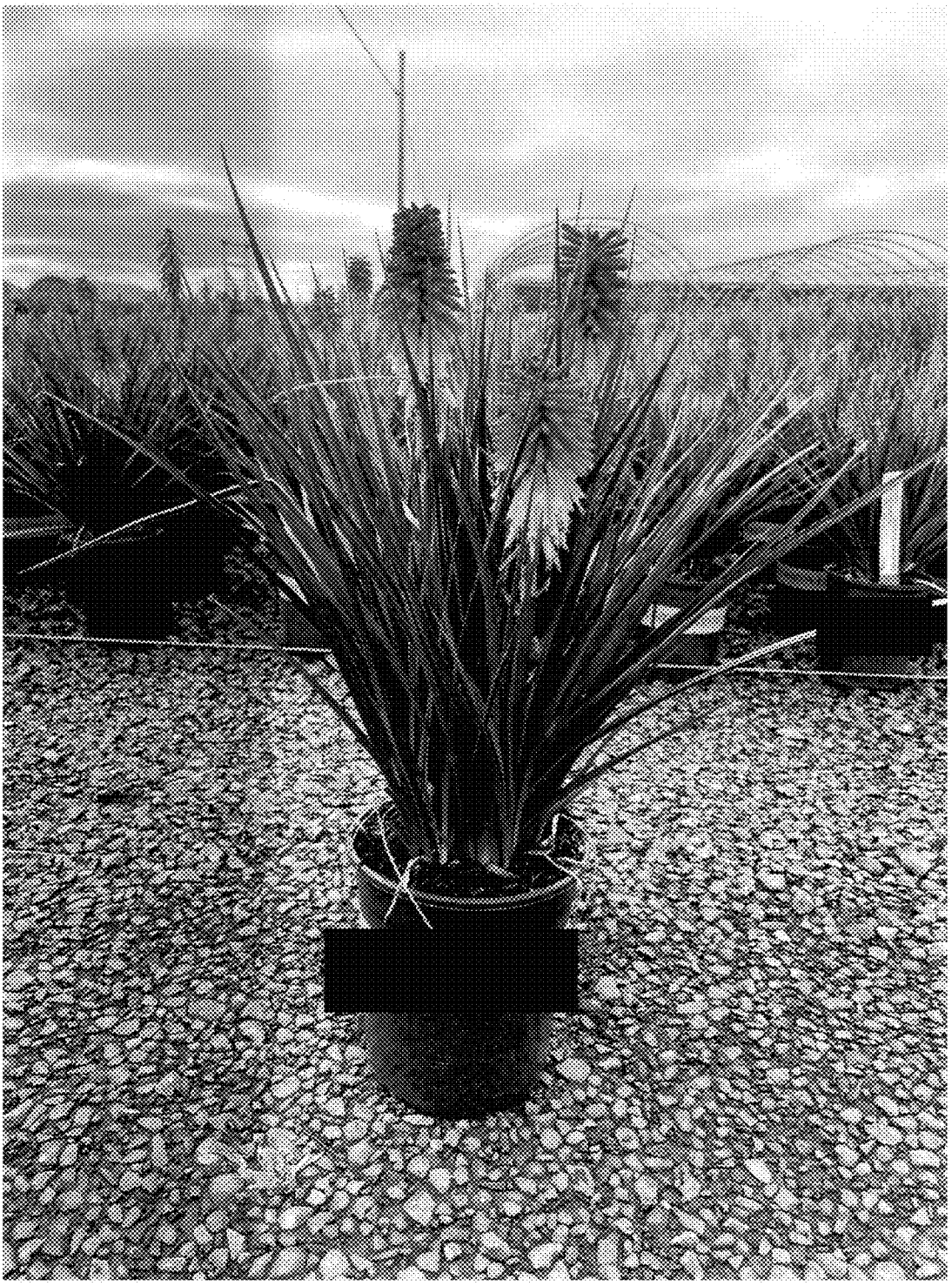
FIG. 2 illustrates an 8-month-old plant of the new variety in Dayton, Oregon in August.

The following is a detailed description of the new variety based on observations of 18-month-old plants in late September that were grown outside in full sun in field conditions in Canby, Oregon (USDA Zone 8). Temperatures range from a high of 35° C. in August to an average of 0° C. in January. Normal rainfall in Canby, Oregon is around 1 m per year. Color references are based on The 2007 R.H.S. Colour Chart of The Royal Horticultural Society of London, 5$^{th}$ Edition.

Plant:

*Type.*—Rhizomatous herbaceous perennial.
*Hardiness.*—USDA Zones 7 to 9.
*Size.*—22.0 to 24.0 cm wide and 38.0 to 40.0 cm tall from the top of the soil to the top of the inflorescences.
*Crown number.*—About 18.
*Leaves per crown.*—About 12.
*Inflorescences per crown.*—1 to 3.
*Form.*—Clumping.
*Vigor.*—Excellent.

Leaf:

*Type.*—Simple.
*Leaf arrangement.*—Basal rosette.
*Shape.*—Strap-like, keeled.
*Length.*—25.0 to 35.0 cm.
*Width.*—6.0 to 8 mm (measured near the base).
*Margin.*—Entire.
*Apex.*—Acuminate.
*Base.*—Clasping.
*Texture.*—Glabrous on both sides.
*Upper surface color.*—RHS 139B.
*Lower surface color.*—RHS 139B.
*Venation.*—Parallel.

Inflorescence:

*Type.*—Spike-like scapose raceme.
*Flower number per raceme.*—About 120 to 130.
*Length.*—16.5 cm.
*Width.*—7.5 cm.
*Bloom period.*—June through October in Canby, Oregon.
*Lastingness.*—From 3-5 weeks on the plant depending on the temperature.
*Peduncle.*—Length: 22.0 cm. Width: 9.0 mm. Texture: Glabrous. Color: RHS N137B.
*Pedicel.*—Length: 2.0 mm. Texture: Glabrous. Color: RHS 173A. Bract: Length: 5.5 mm. Width: 3.0 mm at base of pedicel, narrowing to a point. Texture: Papery and translucent. Color: RHS 145D.

Flower bud:

*Length.*—29.0 mm.
*Width.*—8.0 mm.
*Texture.*—Glabrous.
*Color.*—RHS 169A.

Flower:

*Type.*—Actinomorphic.
*Shape.*—Cylindrical and tubular.
*Depth.*—20.0 mm.
*Width.*—13.0 mm.
*Texure.*—Waxy, with a glabrous surface on both sides.
*Fragrance.*—None.
*Corolla.*—Length: 22.0 mm. Width: 13.0 mm. Arrangement: 6-lobed, fused tepals. Tube size: 22.0 mm long and 7.0 mm wide. Lobes: Shape: Reflexed, ovate, entire, and acute. Size: 4.0 mm long and 4.0 mm wide. Color: Inside RHS 30B, outside RHS N30B on the lower flowers to RHS 18B.
*Pistil.*—Number: 1. Length: 23.0 mm. Ovary size: 2.5 mm long and 1.5 mm wide. Ovary color: RHS 146C. Style length: 22.5 mm. Style color: RHS N167D. Stigma color: RHS 172A.
*Stamen.*—Number: 6. Length: 26.0 mm. Filament length: 25.0 mm. Filament color: RHS 150D. Anther length: 1.0 mm. Anther color: RHS 22A. Pollen amount: Slight. Pollen color: RHS 8C.

Fruit/seeds: No mature fruit formed and no seeds produced.

Pests/diseases: No unusual resistance or susceptibility noted to date.

I claim:

1. A new and distinct variety of *Kniphofia* plant named 'Rocket Jr.', substantially as illustrated and described herein.

* * * * *